(12) United States Patent
Holmes et al.

(10) Patent No.: US 9,121,072 B2
(45) Date of Patent: *Sep. 1, 2015

(54) RAPID SCREENING OF BIOLOGICALLY ACTIVE NUCLEASES AND ISOLATION OF NUCLEASE-MODIFIED CELLS

(75) Inventors: Michael C. Holmes, Oakland, CA (US); Yannick Doyon, El Cerrito, CA (US); Tianjian Li, Benicia, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 180 days.

This patent is subject to a terminal disclaimer.

(21) Appl. No.: 13/234,007

(22) Filed: Sep. 15, 2011

(65) Prior Publication Data

US 2012/0237926 A1 Sep. 20, 2012

Related U.S. Application Data

(63) Continuation of application No. 12/803,552, filed on Jun. 29, 2010, now abandoned, and a continuation-in-part of application No. 12/284,887, filed on Sep. 25, 2008.

(60) Provisional application No. 60/995,566, filed on Sep. 27, 2007, provisional application No. 61/269,871, filed on Jun. 30, 2009.

(51) Int. Cl.
*C12Q 1/68* (2006.01)
*C12N 9/22* (2006.01)

(52) U.S. Cl.
CPC ............... *C12Q 1/6897* (2013.01); *C12N 9/22* (2013.01)

(58) Field of Classification Search
None
See application file for complete search history.

(56) References Cited

U.S. PATENT DOCUMENTS

| | | | |
|---|---|---|---|
| 5,420,032 A | 5/1995 | Marshall et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,534,242 B2 | 3/2003 | Sugita et al. |
| 6,534,261 B1 | 3/2003 | Cox et al. |
| 6,607,882 B1 | 8/2003 | Cox et al. |
| 6,824,978 B1 | 11/2004 | Cox et al. |
| 6,833,252 B1 | 12/2004 | Dujon et al. |
| 6,933,113 B2 | 8/2005 | Case et al. |
| 6,979,539 B2 | 12/2005 | Cox et al. |
| 7,013,219 B2 | 3/2006 | Case et al. |
| 7,163,824 B2 | 1/2007 | Cox et al. |
| 2003/0232410 A1 | 12/2003 | Liljedahl et al. |
| 2004/0002092 A1 | 1/2004 | Arnould et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0078552 A1 | 4/2006 | Arnould et al. |
| 2006/0153826 A1 | 7/2006 | Arnould et al. |
| 2006/0188987 A1 | 8/2006 | Guschin et al. |
| 2006/0206949 A1 | 9/2006 | Arnould et al. |
| 2007/0117128 A1 | 5/2007 | Smith et al. |
| 2007/0134796 A1 | 6/2007 | Holmes et al. |
| 2007/0218528 A1 | 9/2007 | Miller et al. |
| 2008/0131962 A1 | 6/2008 | Miller |
| 2008/0159996 A1 | 7/2008 | Ando et al. |
| 2009/0068164 A1 | 3/2009 | Segal et al. |
| 2009/0111119 A1 | 4/2009 | Doyon et al. |
| 2010/0003756 A1 | 1/2010 | Collingwood et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2004/067753 A2 | 8/2004 |
| WO | WO 2005/014791 A2 | 2/2005 |
| WO | WO 2007/014275 A2 | 1/2007 |
| WO | WO 2007/139898 A2 | 12/2007 |
| WO | WO 2009/042163 A2 | 4/2009 |

OTHER PUBLICATIONS van den Hoff et al. Mammalian gene expression is improved by use of a longer SV40 early polyadenylation cassette. Nucleic Acids Research, vol. 21, No. 21, pp. 4987-4988, 1993.*

(Continued)

*Primary Examiner* — Jennifer Dunston

(74) *Attorney, Agent, or Firm* — Pasternak Patent Law; Susan Abrahamson

(57) ABSTRACT

Disclosed herein are methods and compositions for rapidly identifying active nucleases and cells having nuclease-mediated genomic modifications.

17 Claims, 11 Drawing Sheets

(56) References Cited

OTHER PUBLICATIONS

Liang et al. Template topology and transcription: Chromatin templates relaxed by localized linearization are transcriptionally active in yeast. Molecular and Cellular Biology, vol. 17, No. 5, pp. 2825-2834, May 1997.*
Alwin, et al., "Custom Zinc-Finger Nucleases for Use in Human Cells," *Molecular Therapy 12*:610-617 (2005).
Argast, et al., "I-Ppoi and I-Crei Homing Site Sequence Degeneracy Determined by Random Mutagenesis and Sequential in Vitro Enrichment," *J. Mol. Biol. 280*:345-353 (1998).
Arnould, et al., "Engineering of Large Numbers of Highly Specific Homing Endonucleases That Induce Recombination on Novel DNA Targets," *J Mol Biol 355*:443-458 (2006).
Ashworth, et al., "Computational Redesign of Endonuclease DNA Binding and Cleavage Specificity," *Nature 441*:656-659 (2006).
Beerli, et al., "Engineering Polydactyl Zinc-Finger Transcription Factors," *Nature Biotechnology 20*:135-141 (2002).
Belfort, et al., "Homing Endonucleases: Keeping the House in Order," *Nucleic Acids Research 25*:3379-3388 (1997).
Boch, et al., "Breaking the Code of DNA Binding Specificity of Tal-Type III Effectors," *Science 326*:1509-1512 (2009).
Bonas, et al., "Genetic and Structural Characterization of the Avirulence Gene AVRBS3 From *Xanthomonas campestris* Pv. Vesicatoria," *Mol Gen Genet 218*:127-136 (1989).
Chames, et al., "In Vivo Selection of Engineered Homing Endonucleases Using Double-Strand Break Induced Homologous Recombination," *Nuc Acids Res 33*:e178 (2005).
Chevalier, et al., "Design, Activity, and Structure of a Highly Specific Artificial Endonuclease," *Molecular Cell 10*:895-905 (2002).
Chilton, et al., "Targeted Integration of T-DNA Into the Tobacco Genome at Double-Stranded Breaks: New Insights on the Mechanism of T-DNA Integration," *Plant Physiology 133*:956-965 (2003).
Choo, et al., "Advances in Zinc Finger Engineering," *Curr. Opin. Struct. Biol. 10*:411-416 (2000).
Dujon, et al., "Mobile Introns: Definition of Terms and Recommended Nomenclature," *Gene 82*:115-118 (1989).
Epinat, et al., "A Novel Engineered Meganuclease Induces Homologous Recombination in Yeast and Mammalian Cells," *Nucleic Acids Research 31*:2952-2962 (2003).
Fishman-Lobell, et al., "Removal of Nonhomologous DNA Ends in Double-Strand Break Recombination: The Role of the Yeast Ultraviolet Repair Gene RAD1," *Science 258*:480-484 (1992).
Gimble, et al., "Substrate Recognition and Induced DNA Distortion by the PI-SCEI Endonuclease, an Enzyme Generated by Protein Splicing," *J. Mol. Biol. 263*:163-180 (1996).
Gouble, et al., "Efficient in Toto Targeted Recombination in Mouse Liver by Meganuclease-Induced Double-Strand Break," *J Gene Med 8*:616-622 (2006).
Heuer, et al., "Repeat Domain Diversity of AVRBS3-Like Genes in *Ralstonia* Solanacearum Strains and Association With Host Preferences in the Field," *Appl and Envir Micro 73*:4379-4384 (2007).
Isalan et al., "A Rapid, Generally Applicable Method to Engineer Zinc Fingers Illustrated by Targeting the HIV-1 Promoter," *Nat Biotechnol 19*:656-660 (2001).
Jasin, et al., "Genetic Manipulation of Genomes With Rare-Cutting Endonucleases," *Trends Genet 12*:224-228 (1996).
Kim, et al., Hybrid Restriction Enzymes: Zinc finger fusions to Fokl cleavage domain. Biochemistry. 93:156-1160 (1996).
Maeder, et al., "Oligomerized Pool Engineering (Open): An "Open-Source" Protocol for Making Customized Zinc Finger Arrays," *Nature Protocols 4*:1471-1501 (2009).
Maxwell, et al., "Inefficiency of Expression of Luciferase Reporter From Transfected Murine Leukaemia Proviral DNA May Be Partially Overcome by Providing a Strong Polyadenylation Signal," *Journal of General Virology 72*:1721-1724 (1991).
Miller, et al., "An Improved Zinc-Finger Nuclease Architecture for Highly Specific Genome Editing," *Nature Biotech 25*:778-785 (2007).
Moehle, et al., "Targeted Gene Addition Into a Specified Location in the Human Genome Using Designed Zinc Finger Nucleases," *PNAS 104*:3055-3060 (2006).
Monnat, et al., "Generation of Highly Site-Specific DNA Double-Strand Breaks in Human Cells by the Homing Endonucleases I-Ppoi and I-Crei," *Biochem Biophysics Res Common 255*:88-93 (1999).
Moscou, et al., "A Simple Cipher Governs DNA Recognition by Tal Effectors," *Science 326*:1501 (2009).
Pabo, et al., "Design and Selection of Novel CYS2-HIS2 Zinc Finger Proteins," *Ann. Rev. Biochem. 70*:313-340 (2001).
Paques, et al., "Meganucleases and DNA Double-Strand Break-Induced Recombination: Perspectives for Gene Therapy," *Current Gene Therapy 7*:49-66 (2007).
Perez, et al., "Factors Affecting Double-Strand Break-Induced Homologous Recombination in Mammalian Cells," *BioTechniques 39*:109-115 (2005).
Perez, et al., "Establishment of HIV-1 Resistance in CD4+ T Cells by Genome Editing Using Zinc-Finger Nucleases," *Nature Biotechnology 26*:808-816 (2008).
Perler, et al., "Protein Splicing Elements: Inteins and Exteins a Definition of Terms and Recommended Nomenclature," *Nucleic Acids Research 22*:1125-1127 (1994).
Porteus, et al., "Gene Targeting Using Zinc Finger Nucleases," *Nature Biotechnology 23*:967-973 (2005).
Puchta, et al., "Two Different But Related Mechanisms Are Used in Plants for the Repair of Genomic Double-Strand Breaks by Homologous Recombination," *PNAS USA 93*:5055-5060 (1996).
Rong, et al., "Targeted Mutagenesis by Homologous Recombination in D. Melanogaster," *Genes & Dev 16*:1568-1581 (2002).
Rouet, et al., "Introduction of Double-Strand Breaks Into the Genome of Mouse Cells by Expression of a Rare-Cutting Endonuclease," *Molecular and Cellular Biology 14*:8096-8106 (1994).
Schornack, et al., "Gene-For-Gene-Mediated Recognition of Nuclear-Targeted AVRBS3-Like Bacterial Effector Proteins," *J Plant Physiol 163*:256-272 (2006).
Segal, et al., "Custom DNA-Binding Proteins Come of Age: Polydactyl Zinc-Finger Proteins," *Curr. Opin. Biotechnol. 12*:632-637 (2001).
Sussman, et al., "Isolation and Characterization of New Homing Endonuclease Specificities at Individual Target Site Positions," *J Mol Biol 342*:31-41 (2004).
Urnov, et al., "Highly Efficient Endogenous Human Gene Correction Using Designed Zinc-Finger Nucleases," *Nature 435*:646-651 (2005).
Cai, et al., "Targeted Transgene Integration in Plant Cells Using Designed Zinc Finger Nucleases," *Plant Mol Biol 69*:699 -709 (2009).
Porteus, et al., "Mammalian Gene Targeting With Designed Zinc Finger Nucleases," *Molecular Therapy 13*:438-446 (2006).
Porteus, et al., "Design and Testing of Zinc Finger Nucleases for Use in Mammalian Cells," *Methods in Molecular Biology*, pp. 47-61, Humana Press (2008).
Wu, et al., "Custom-Designed Zinc Finger Nucleases: What Is Next?" *CMLS 64*:2933-2944 (2007).

* cited by examiner

RAPID SCREENING OF BIOLOGICALLY ACTIVE NUCLEASES AND ISOLATION OF NUCLEASE-MODIFIED CELLS

CROSS-REFERENCE TO RELATED APPLICATIONS

The present application is a continuation of U.S. patent application Ser. No. 12/803,552, filed Jun. 29, 2010, now abandoned, which claims the benefit of U.S. Provisional Application No. 61/269,871, filed Jun. 30, 2009. The present application is also, a continuation-in-part of U.S. patent application Ser. No. 12/284,887, filed Sep. 25, 2008, which claims the benefit of U.S. Provisional Application No. 60/995,566, filed Sep. 27, 2007. All of the above-referenced applications are incorporated herein in their entireties.

STATEMENT OF RIGHTS TO INVENTIONS MADE UNDER FEDERALLY SPONSORED RESEARCH

Not applicable.

TECHNICAL FIELD

The present disclosure is in the fields of genome engineering and nuclease identification.

BACKGROUND

Nucleases, including zinc finger nucleases and homing endonucleases such as I-SceI, that are engineered to specifically bind to target sites have been shown to be useful in genome engineering in basic research and in the pharmaceutical and biotechnology applications. For example, zinc finger nucleases (ZFNs) are proteins comprising engineered site-specific zinc fingers fused to a nuclease domain. Such ZFNs have been successfully used for genome modification in a variety of different species. See, for example, United States Patent Publications 20030232410; 20050208489; 20050026157; 20050064474; 20060188987; 20060063231; and International Publication WO 07/014,275, the disclosures of which are incorporated by reference in their entireties for all purposes. These ZFNs can be used to create a double-strand break (DSB) in a target nucleotide sequence, which increases the frequency of homologous recombination at the targeted locus (targeted integration) more than 1000-fold. In addition, the inaccurate repair of a site-specific DSB by non-homologous end joining (NHEJ) can also result in gene disruption. Creation of two such DSBs results in deletion of arbitrarily large regions.

As nuclease-mediated genome modification facilitates basic science research and development of therapeutics, in vitro and in vivo assays have been developed to measure the activity of ZFNs. See, e.g., WO 2009/042163. These assays are based on different pathways to repair DNA double-strand breaks (DSBs) catalyzed by the recruitment of ZFNs to a pre-determined location in the genome of eukaryotic cells. DSB are repaired by either non-conservative non-homologous end-joining (NHEJ) pathways or the conservative homology directed repair (HDR). In addition, a non-conservative HDR pathway called single-strand-annealing (SSA) is also present in most cells. The SSA pathway shares some of the cellular machinery with the HR pathway.

In addition to detecting biologically active nucleases by measuring their increased capacity to bind and cleave their intended loci in the genome, it is also desirable to identify and enrich for cells having the desired nuclease-mediated genomic modifications. Currently, many existing methods rely on the integration and expression of a drug selection marker into the desired locus. The marker and/or drug selection genes are often integrated into the cell genome permanently or exist in an episomal form for a long period of time. The presence of these genetic elements in the final cell clone is often undesirable. Also, the high incidence of random integration can create a high background of cell clones with no modification at the intended target locus.

Thus, there remains a need for additional assays to screen for nuclease activity and to identify cells with the desired genomic modifications without using drug selection or a permanent marker that is integrated into the genome.

SUMMARY

Described herein are methods and compositions for screening nuclease (e.g., ZFN) activity and for efficient enrichment of cell lines or clones genomically modified at an endogenous locus without drug selection or the use of markers that become permanently integrated in the genome. The assays make use of a nuclease that cuts at a site (e.g., an engineered site) in a disabled gene, preferably a reporter gene. The disabled gene is preferably episomal (i.e., located within a construct that is not within the endogenous locus). Cleavage by the nuclease at the engineered site allows the homologous regions to repair and reconstitute the disabled gene via SSA. The engineered site within the disabled gene has the same sequence as a target site within an endogenous target locus where cleavage is desired, such that cleavage at the endogenous site occurs when the disabled reporter gene of the construct is cleaved. Thus, the relative efficiency of SSA repair correlates well with relative efficiency of nuclease activity at the endogenous target locus. Also, individual cells that carry out SSA-mediated repair in assays as described herein show increased modification at the endogenous target locus thus, allowing for the rapid identification of cells with the desired genomic modification(s). The methods and compositions described herein significantly alleviate the obstacles associated with integration of selection or other markers into the genome.

In one aspect, described herein is a reporter construct for detecting SSA mediated cleavage of a target sequence by one or more nucleases. The reporter construct comprises a sequence encoding a gene and a sequence comprising one or more target sites for a nuclease inserted within the sequence encoding the gene such that the gene is non-functional (disabled) until the target site(s) is (are) cleaved and repaired by SSA. Following cleavage of the target site(s), the sequence encoding the gene is recreated by SSA and gene function restored.

Thus, in certain embodiments, the reporter construct comprises, in a 5' to 3' direction, a first nucleotide sequence encoding a first portion of a reporter gene, a second nucleotide sequence encoding a second portion of the reporter gene, a sequence comprising one or more target sequences for a nuclease, a third nucleotide sequence encoding the second portion of the reporter gene and a fourth nucleotide sequence encoding a third portion of the reporter gene. The first, second and third portions of the reporter gene encode the functional reporter gene. Any of the reporter constructs described herein may further comprise a polyadenylation signal and/or a promoter (e.g., a constitutive promoter) operably linked the reporter gene. Furthermore, the reporter gene can encode a light-generating protein (e.g. GFP), an enzyme, a cell surface receptor, and/or a selectable marker.

In another aspect, the invention provides a host cell comprising any of the reporter constructs described herein. In certain embodiments, the cell is a eukaryotic cell (e.g., a mammalian cell). The reporter construct may be transiently or stably expressed in the host cell. Any of the host cells may further comprise a sequence encoding a nuclease, for example a homing nuclease, a zinc finger nuclease or a nuclease comprising a TAL-effector domain fused to a nuclease domain.

In yet another aspect, provided herein is a method of identifying one or more nucleases that induce cleavage at a specific target site, the method comprising the steps of: introducing one or more expression constructs that express the nuclease(s) into any of the host cells described herein, wherein the reporter construct comprises a target sequence recognized by the nuclease; incubating the cells under conditions such that the nuclease is expressed; and measuring the levels of reporter gene expression in the cells, wherein increased levels of reporter gene expression are correlated with increased nuclease-induced cleavage of the target sequence.

In yet another aspect, methods of identifying a nuclease that induces cleavage at a specific target site are provided. In certain embodiments, the methods comprise introducing one or more nucleases and/or one or more nuclease-expression constructs encoding a nuclease or a pair of nucleases into a host cell comprising a reporter construct as described herein, the reporter construct comprising a target sequence recognized by the nuclease(s); incubating the cells under conditions such that the nuclease(s) are expressed; and measuring the levels of reporter gene expression in the cells, wherein increased levels of reporter gene expression are correlated with increased nuclease-induced cleavage of the target sequence. The nuclease may comprise, for example, a non-naturally occurring DNA-binding domain (e.g., an engineered zinc finger protein, an engineered DNA-binding domain from a homing endonuclease, or an engineered nuclease comprising a fusion between a TAL-effector domain and a nuclease domain). In certain embodiments, the nuclease is a zinc finger nuclease (ZFN) or pair of ZFNs.

In a still further aspect, the invention includes a method of enriching a population of cells for cells having a nuclease-mediated genomic modification, the method comprising the steps of: introducing one or more expression constructs encoding a nuclease or a pair of nucleases into host cells as described herein, wherein the reporter construct in the host cells comprises a target sequence recognized by the nuclease; incubating the cells under conditions such that the nucleases are expressed; measuring the levels of reporter gene expression in the cells; and selecting cells that express the reporter gene, thereby enriching the population of cells for cells with nuclease-mediated genomic modifications. Further still, a panel of nucleases may be compared simultaneously that all recognize the same target sequence. The panel may be transfected along with the SSA reporter in parallel, providing a rapid indication and ranking of activity of those nucleases within the test panel. Any of the methods may further comprise introducing an exogenous sequence into the host cell such that the nuclease mediates targeted integration of the exogenous sequence into the genome. In certain embodiments, the methods further comprise isolating the cells expressing the reporter gene. In any of the methods described herein, the genomic modification is a gene disruption and/or a gene addition.

In any of the methods described herein, reporter gene activity may be measured directly, for example by directly assaying the levels of the reporter gene product activity (e.g., GFP fluorescence). Likewise, cells expressing the reporter gene may be isolated or selected based on direct selection, for example FACS in the case of a reporter such as GFP or using fluorescent ligands directed to a reporter gene encoding a cell surface protein or receptor. Magnetic sorting can also be employed. When the reporter is a drug selection marker, drug selection may also be used to select cells. Alternatively, levels of the reporter gene can be assayed by measuring or selecting based on the levels of a downstream product (e.g., enzymatic product) of the reaction that requires function of the protein encoded by the reporter gene.

Furthermore, in any of the methods described herein, the nuclease(s) (e.g., ZFN, ZFN pair, engineered homing endonuclease and/or fusion or a naturally occurring or engineered homing endonuclease DNA-binding domain and heterologous cleavage domain, or a nuclease comprising a fusion between a TAL-effector domain and a nuclease domain) may be known to recognize the endogenous target sequence, for example from results obtained from in vitro assay experiments. In another aspect, described herein is a kit for screening a nuclease (e.g., zinc finger protein, engineered homing endonuclease, or a nuclease comprising a fusion between a TAL-effector domain and a nuclease domain) for activity, the kit comprising a reporter construct as described herein; ancillary reagents; and optionally instructions and suitable containers. The kit may also include one or more nucleases.

In yet another aspect, described herein is a kit for preparing cells having nuclease-mediated genomic modifications, the kit comprising a reporter construct as described herein and a nuclease that recognizes a target site in the reporter construct; and optionally instructions and suitable containers.

Any of the kits described herein may comprise at least the construct with the disabled gene and a known nuclease capable of cleaving within the disabled gene at a known engineered site. Such kits are useful for optimization of cleavage conditions. Other such kits may provide constructs wherein the user may insert the engineered site of interest for use in identifying and/or screening nucleases capable of cleavage at such an engineered site. In some embodiments, the disabled gene is a screening marker (e.g. GFP), while in other embodiments, the disable gene is a selection marker such as one encoding antibiotic resistance. In still further embodiments, the disabled gene encodes a cell surface marker or receptor wherein following reconstitution via SSA, the reporter is expressed on the cell surface and can be used to identify those clones wherein SSA mediated gene reconstitution has occurred (e.g., via FACS or magnetic bead sorting). In all kits contemplated by the invention, the reporter gene may be operatively linked to a polyadenylation signal and/or a regulatory element (e.g. a promoter). Such kits provided for by the instant invention may be useful for optimization of assay conditions, screening panels of nucleases or for the characterization of known nucleases.

BRIEF DESCRIPTION OF THE DRAWINGS

FIG. 1, panels A to D, depict SSA reporter assay optimization in CHO-S cells.

FIG. 4A shows results of Cel-I assays performed in HeLa cells treated with GFP plasmid alone (G), or transfected with the ZFN and GFP-SSA reporter constructs, where samples were either analyzed prior to sorting (U), or following sorting based on GFP activity (S). FIG. 4B shows enrichment of NHEJ activity in PBMC cells. A0 through A4 are samples transduced with adenovirus reporters only. B1 through B4 are samples transduced with CCR5-specific ZFNs and the GFP-SSA adenovirus reporters. Percent NHEJ activity is shown for lanes B1-B4. FIG. 4C shows results in PBMC cells transduced with adenoviruses expressing CCR5-specific ZFNs and a GFP-SSA reporter and sorted by FACS according to GFP expression (samples designated B1 to B4 as shown in FIG. 4B). The highest GFP expressers were differentially gated and collected for Cel-I analysis. Percent NHEJ activities of the indicated samples is shown at the bottom of each lane. This data demonstrates that the cells with the highest GFP expression also had high percentages of NHEJ.

FIG. 5A shows NHEJ activity before and after FACS sorting. Cel-I analysis was performed on mock (C), reporter (R), and ZFN and GFP-SSA reporter construct transfected sample, either sorted (S), or unsorted (U). Lane 1 is marker (M). FIG. 5B shows targeted integration of a patch donor before and after FACS sorting. Targeted integration was measure by PCR based-RFLP analysis on an engineered BglII site on the patch donor. Mock transfections are shown in the lane labeled "C," while reporter construct only transfections are shown in the lane labeled "R." ZFN and reporter transfected samples, either sorted (S), or unsorted (U) are also shown. Lanes 6 and 7 are markers (M). FIG. 5C depicts results of a targeted integration (TI) clonal analysis. Lane numbers are indicated below. Individual clones were isolated, expanded and subjected to PCR based-RFLP analysis. Lane 1 is marker (M); Lane 3 is a heterozygous clone. Lane 4 and 6 are clones with all alleles modified. (K). Lane 3 is a heterozygous clone (H). Lane 5 is a wild type clone (W). Lane 7 (P) is the pool activity before sorting. This data demonstrates that the cells with the highest GFP expression also had high percentages of targeted integration.

FIG. 7A depicts Southern analysis of genomic DNA from Factor IX ZFN modified clones digested with PvuII and probed with the 146 bp of 5' unique gfp sequence. Lane "R" show 1 ng of reporter plasmids digested with PvuII. The main signal in Lane R is the 5.8 kb fragment of the reporter. The white arrow points to lower weaker band that is likely the 4.0 kb fragment of the recombined reporter plasmid. The black arrows indicate bands of integrated gfp sequence in these clones. In clone 106, the horizontal white arrow indicates the episomal form of the recombined reporter plasmid. FIG. 7B depicts PCR analysis of genomic DNA from Factor IX ZFN modified clones. The amplicon is a 146 bp fragment of the 5' unique gfp sequences. Lane 7 is the clone that retained gfp signal 41 days after transfection.

DETAILED DESCRIPTION

Figure 1A:
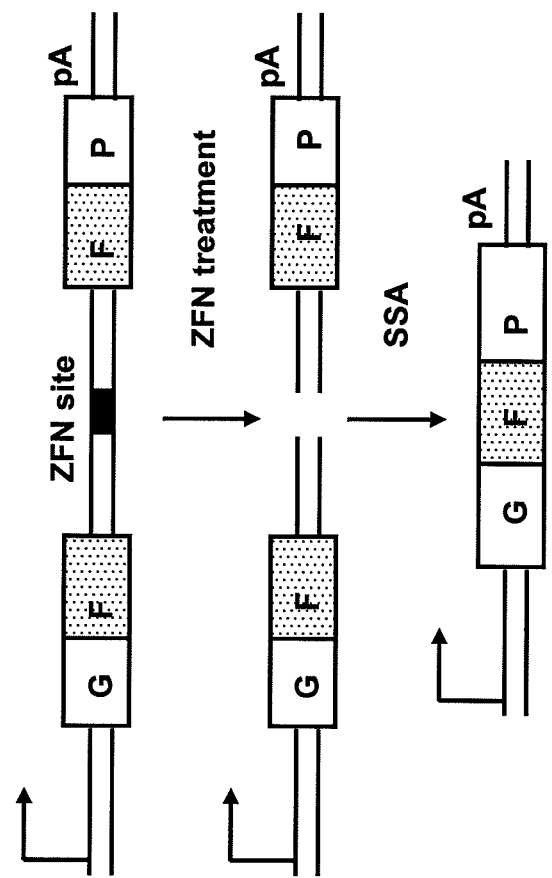
FIG. 1A is a diagram of single strand annealing based ZFN screening assay (SSA assay). The top line shows a reporter plasmid including a ZFN site which disrupts (disables) the reporter GFP gene. The arrow indicates promoter sequence and "pA" refers to a polyA sequence. The unique 5' gfp sequence, middle repeated gfp sequence, and unique 3'gfp sequence are designated as G, F, and P respectively. Following cleavage with the appropriate nuclease(s) and SSA-mediated repair (middle and bottom lines), the functional gfp open reading frame is reconstituted by loss of sequences between the two identical 5' and 3' F sequences.

Described herein are compositions and methods for high throughput in vivo screening systems for identifying functional nucleases and kits comprising the compositions described herein and for carrying out the methods described herein. In particular, the assays use a reporter system to monitor the ability of a nuclease to induce a double-stranded break at a target site. In addition, the compositions and methods described herein can also be used to screen panels of nucleases to identify those with the highest activity, to optimize nuclease cleavage conditions and to rapidly enrich for modified cell lines or clones that have undergone nuclease-induced gene disruption and/or gene addition.

Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs have been attached to nuclease domains to create ZFNs—a functional entity that is able to recognize its intended gene target through its engineered (ZFP) DNA binding domain and the nuclease causes the gene to be cut near the ZFP binding site. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275.

TAL-effector DNA binding domains, isolated from the plant pathogen Xanthomonas have recently been described (see Boch et al, (2009) Science 29 Oct. 2009 (10.1126/science.117881) and Moscou and Bogdanove, (2009) Science 29 Oct. 2009 (10.1126/science.1178817)). These DNA binding domains may be engineered to bind to a desired target and fused to a nuclease domain (e.g. Fok1) to derive a TAL effector domain-nuclease fusion protein. Thus, the methods and compositions of the invention may be used with TAL-effector DNA binding domain-nuclease fusion proteins to screen for activity and other characteristics of interest.

The identification of biologically active nucleases is not always accurately predicted using in vitro assays. Accordingly, assays have been developed for evaluating nucleases in vivo. See, e.g., WO 2009/042163. However, these assays function most efficiently when the reporter construct is stably integrated into the genome of the host cell. As such, cells with nuclease-only genomic modifications (i.e., no integrated reporter) cannot readily be identified or isolated. In addition, not all biological systems have readily available or experimentally tractable cell lines for easy or robust screening.

Furthermore, since every in vivo system has its own peculiarities, it is necessary to develop specific detection assays to determine ZFN action. Thus, unlike previously described in vivo screening methods which screen for homing endonucleases with binding specificity different from the naturally occurring homing endonuclease, the methods described herein provide a rapid and efficient way of evaluating nucleases known to bind to a particular target site for their in vivo functionality as well as the ability to rapidly identify and isolate cells with the desired nuclease-mediated genomic modifications.

Thus, the methods and compositions described herein provide highly efficient and rapid methods for identifying nucleases that are biologically active in vivo. In addition to accurately predicting in vivo nuclease functionality, the assays described herein also can be used to screen for and isolate nuclease-modified cells that do not contain an integrated reporter construct. These methods and compositions also allow the ranking of the most active nucleases in cells simply through the measurement of a reconstituted reporter gene's activity. The methods and compositions described herein also provide the components for kits to allow screening, optimization and characterization of nucleases within a cell.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains (e.g., the recognition helix region) can be "engineered" to bind to a predetermined nucleotide sequence. The engineered region of the zinc finger is typically the recognition helix, particularly the portion of the alpha-helical region numbered −1 to +6. Backbone sequences for an engineered recognition helix are known in the art. See, e.g., Miller et al. (2007) *Nat Biotechnol* 25, 778-785. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

A "TAL-effector repeat sequence" is the structural sequence that is involved in the binding of the TAL-effector to its cognate target DNA sequence. These repeats are typically 34 amino acids in length and almost invariably exhibit a great deal of sequence homology with other TAL-effector repeat sequences within a TAL-effector protein. Positions 12 and 13 exhibit hypervariability and are thought to be the amino acids that determine what DNA nucleotide the repeat will interact with. The identity of these amino acids largely determine the DNA base the repeat sequence interacts with. The most C-terminal repeat often displays sequence similarity only for the first 20 amino acids and so is sometimes referred to as a half repeat. The most N-terminal repeat has a sequence immediately preceding it that shows similarity to the repeat sequences on a structural level, and thus is termed the R0 repeat.

A "TAL-effector DNA binding domain" is a protein, or a domain within a larger protein, that interacts with DNA in a sequence-specific manner through one or more tandem repeat domains.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

Zinc finger DNA binding domains or TAL-effector DNA binding domains can be "engineered" to bind to a predetermined nucleotide sequence, for example via engineering (altering one or more amino acids) of the hypervariable diresidue region at positions 12 and 13 of a naturally repeat domain within a TAL-effector protein or by engineering the DNA binding portion of the DNA recognition helix of a zinc finger protein. Therefore, engineered zinc finger proteins and TAL-effector proteins are proteins that are non-naturally occurring. Non-limiting examples of methods for engineering zinc finger proteins and TAL-effector proteins are design and selection. A designed zinc finger protein or TAL-effector protein is a protein not occurring in nature whose design/composition results principally from rational criteria. Rational criteria for design include application of substitution rules and computerized algorithms for processing information in a database storing information of existing zinc finger protein or TAL-effector designs and binding data.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain or a fusion between a TAL-effector DNA binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. A similar example is where a TAL-effector DNA binding domain is operatively linked to a cleavage domain such that cleavage of DNA occurs in the vicinity of the target site of the TAL effector DNA binding domain.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

Overview

Described herein are compositions and methods for the in vivo identification of nucleases that cleave their target sites with the highest frequency. The compositions and methods described herein can also be used to isolate cells having the desired genomic modifications, but without an integrated reporter. In the methods described herein, the reporter construct comprising the target site(s) for the nuclease(s) is introduced into a host cell. When the nuclease(s) are expressed in the cell and induce a double stranded break (DSB) at their target site (e.g., induce a double-stranded break), the reporter gene is reconstituted by the host cell's single-stranded annealing (SSA) machinery. Expression of the reporter gene is readily determined by standard techniques and the levels of reporter gene expression reflect the ability of the nuclease to cleave at the target site. In addition, the SSA reporter systems accurately assess ZFN, meganuclease or TAL-effector domain nuclease fusion protein activity on the endogenous target site and, accordingly, sorting cells for nuclease-mediated expression of the SSA reporter allows for high throughput screening and isolation of nuclease (e.g., ZFN, meganuclease or TAL-effector domain nuclease fusion protein)-modified cells.

Thus, described herein are rapid and efficient high throughput screening and isolation methods for determining the active nucleases and selecting cells with the desired genomic modifications. Accordingly, the compositions and methods described herein can also be utilized in kits that allow the user to screen nucleases and to select cells with desired genomic modifications.

Reporter Constructs

The methods and systems described herein make use of a reporter construct comprising a sequence containing a target sequence for the nuclease(s) to be tested. The reporter construct is designed so that the reporter gene becomes functional only when the nuclease cleaves the target sequence and the reporter gene is reconstituted by single-strand annealing (SSA) repair mechanisms.

Typically, a reporter construct is generated such that any nuclease target sequence(s) can be readily inserted into the middle of the disabled reporter gene sequence (see, FIG. 1A). Preferably, the target sequences are inserted between two identical partial sequences of the reporter gene. The two identical partial sequences on either site of the nuclease target site are flanked by unique 3' and 5' coding regions of the reporter gene. Following cleavage of the target site and SSA repair mechanisms, the sequences between the two identical partial sequences are lost and the reporter gene reconstituted in a functional open reading frame. See, FIG. 1A.

One or more target sites for the nuclease(s) to be screened can be inserted into the reporter constructs by any suitable methodology, including PCR or commercially available cloning systems such as TOPO® and/or Gateway® cloning systems. In certain embodiments, the target site comprises a concatamer of target sites. Target sites can be from prokaryotic or eukaryotic genes, for example, mammalian (e.g., human), yeast or plant cells. It is preferred, but not required, that the target site(s) in the reporter constructs be present in the genome of the host cell.

Any reporter gene can be used in the SSA constructs described herein. In certain embodiments, the reporter gene provides a directly detectable signal directly, for example, a signal from a fluorescent protein such as, for example, GFP (green fluorescent protein). Fluorescence is detected using a variety of commercially available fluorescent detection systems, including, e.g., a fluorescence-activated cell sorter (FACS) system. Reporter genes may also be enzymes that catalyze the production of a detectable product (e.g. proteases, nucleases, lipases, phosphatases, sugar hydrolases and esterases). Non-limiting examples of suitable reporter genes that encode enzymes include, for example, MEL1, CAT (chloramphenicol acetyl transferase; Alton and Vapnek (1979) *Nature* 282:864 869), luciferase, β-galactosidase, β-glucuronidase, β-lactamase, horseradish peroxidase and alkaline phosphatase (e.g., Toh, et al. (1980) *Eur. J. Biochem.* 182:231 238; and Hall et al. (1983) *J. Mol. Appl. Gen.* 2:101).

Additional reporter genes include cell-surface based markers (e.g., receptors) that can be enriched for by either FACS or antibody-coated magnetic beads as well as drug-based selection markers (e.g., antibiotic resistance such as ampicillin resistance, neomycin resistance, G418 resistance, puromycin resistance). Magnetic beads carrying ligands for cell surface receptors or carrying compounds capable of interacting with cell surface receptors can be used with the methods of the invention. For example, commercially available nickel charged magnetic beads can be used to enrich cells in which a reconstituted cell surface protein contains a His tag. Alternatively, commercially available magnetic cyanogen bromide beads can be activated to bind to a ligand of choice and then used in the methods described herein to enrich or purify cells containing a reconstituted SSA cell surface reporter protein.

The reporter construct typically includes a promoter that drives expression of the reporter gene upon cleavage by the nuclease and subsequent SSA-mediated repair of a functional reporter. Any suitable promoter can be used, preferably a promoter that functional in the host cell. Preferably the promoter is a constitutive promoter such as CMV, although in certain cases inducible promoters may be employed. A polyadenylation signal may also be included in the reporter construct (see, e.g., FIG. 1A).

Host Cells

Any host cell that reconstitutes a functional reporter upon cleavage of the target sequence by the nuclease(s) can be used in the practice of the present disclosure. The cell types can be cell lines or natural (e.g., isolated) cells such as, for example, primary cells. Cell lines are available, for example from the American Type Culture Collection (ATCC), or can be generated by methods known in the art, as described for example in Freshney et al., Culture of Animal Cells, A Manual of Basic Technique, 3rd ed., 1994, and references cited therein. Similarly, cells can be isolated by methods known in the art. Other non-limiting examples of cell types include cells that have or are subject to pathologies, such as cancerous cells and transformed cells, pathogenically infected cells, stem cells, fully differentiated cells, partially differentiated cells, immortalized cells and the like. Prokaryotic (e.g., bacterial) or eukaryotic (e.g., yeast, plant, fungal, piscine and mammalian cells such as feline, canine, murine, bovine, porcine and human) cells can be used, with eukaryotic cells being preferred. Suitable mammalian cell lines include K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) *J. Gen. Virol.* 36:59), and myeloma cells like SP2 or NS0 (see, e.g., Galfre and Milstein (1981) Meth. Enzymol. 73(B):3 46). Peripheral blood mononucleocytes (PBMCs) or T-cells can also serve as hosts. Other eukaryotic cells include, for example, insect (e.g., sp. *frugiperda*), fungal cells, including yeast (e.g., *S. cerevisiae, S. pombe, P. pastoris, K. lactis, H. polymorpha*), and plant cells (Fleer, R. (1992) *Current Opinion in Biotechnology* 3:486 496).

Nucleases

The methods and compositions described herein are broadly applicable and may involve any nuclease of interest. Non-limiting examples of nucleases include meganucleases and zinc finger nucleases. The nuclease may comprise heterologous DNA-binding and cleavage domains (e.g., zinc finger nucleases; meganuclease DNA-binding domains with heterologous cleavage domains or TAL-effector domain nuclease fusions) or, alternatively, the DNA-binding domain of a naturally-occurring nuclease may be altered to bind to a selected target site (e.g., a meganuclease that has been engineered to bind to site different than the cognate binding site or a TAL-effector domain nuclease fusion).

In certain embodiment, the nuclease is a meganuclease (homing endonuclease). Naturally-occurring meganucleases recognize 15-40 base-pair cleavage sites and are commonly grouped into four families: the LAGLIDADG (SEQ ID NO:1) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family, have been used to promote site-specific genome modification in plants, yeast, Drosophila, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In some embodiments, the nuclease is a TAL-effector domain nuclease fusion. One of the most well characterized TAL-effectors is AvrBs3 from Xanthomonas campestgris pv. Vesicatoria (see Bonas et al (1989) *Mol Gen Genet* 218: 127-136). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brgl 1 and hpx17 have been found that are homologous to the AvrBs3 family of Xanthomonas in the *R. solanacearum* biovar 1 strain GMI1000 and in the biovar 4 strain RS1000 (See Heuer et al (2007) *Appl and Envir Micro* 73(13): 4379-4384). Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hyperviariable diresidues at positions 12 and 13 with the identity of the contiguous nucleotides in the TAL-effector's target sequence (see Moscou and Bogdanove, (2009) *Science* 326:1501 and Boch et al (2009) *Science* 326: 1509-1512). Thus, TAL-effector domains can be fused to a cleavage domain (e.g. FokI) to create a TAL-effector domain nuclease fusion protein which can be used with the methods and compositions of the invention. In other embodiments, the nuclease is a zinc finger nuclease (ZFN). ZFNs comprise a zinc finger protein that has been engineered to bind to a target site in a gene of choice and cleavage domain or a cleavage half-domain.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Nucleases such as ZFNs and/or meganucleases and/or TAL-effector domain fusions also comprise a nuclease (cleavage domain, cleavage half-domain). As noted above, the cleavage domain may be heterologous to the DNA-binding domain, for example a zinc finger DNA-binding domain and a cleavage domain from a nuclease, a meganuclease DNA-binding domain and cleavage domain from a different nuclease or a TAL-effector domain-nuclease fusion. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→*K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

The engineered cleavage half-domains described herein can be obligate heterodimer mutants in which aberrant cleavage is minimized or abolished. See, e.g., Example 1 of WO 07/139,898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. provisional application 61/337,769 filed Feb. 8, 2010).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs) can be screened for activity prior to use, for example in a yeast-based chromosomal system as described in WO 2009/042163.

Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Kits

Also provided are kits for performing any of the above methods. The kits typically contain one or more reporter constructs as described herein, each reporter containing a cloning site for insertion of the target site for a nuclease of interest. For example, kits for screening nucleases with activity to a particular gene are provided with one or more reporter constructs containing the desired target site(s). Similarly, kits for enriching cells for a population of cells having a nuclease-mediated genomic modification comprise a reporter construct comprising a target site present in the genome of the cells and one or more nuclease specific to the target site of interest.

The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed methods and compositions can be used for rapid identification of nucleases that are active on their endogenous targets without integration of the reporter construct into the genome of any host cell. Identification of such nucleases begins with the generation of a reporter construct, preferably episomal, which is configured with the nuclease (e.g., ZFN) binding site(s) inserted between 2 stretches of homologous reporter sequences. Cleavage by the nuclease allows the 2 homologous sequences to repair and reconstitute a functional reporter via SSA. The relative efficiency of this repair that allows the expression of the reporter correlates well with relative efficiency of nuclease activity at the endogenous target locus. Thus, the methods and compositions described herein allow for high-throughput screening of active nucleases.

In addition, the compositions and methods described herein allow for efficient isolation of cells containing nuclease-modified genomes. Cells that carryout SSA-mediated repair of the episomal plasmid-based or viral-based (e.g. adenoviral, AAV or lentiviral derived) reporter also show an increased level of modification at the endogenous target locus, including both NHEJ activities and as well as targeted integration of donor sequences. Accordingly, modified cell clones can be efficiently isolated following enrichment using the reconstituted SSA marker by selecting cells expressing the reporter gene. For example, fluorescence activated cell sorting (FACS) can be used to select cells expressing a reconstituted GFP reporter. Furthermore, very high percentages of cells selected for expression of the repaired marker are modified (gene disruption or gene addition) at all copies of the target gene, thus providing a method of efficiently isolating cell clones with all copies of the target gene disrupted. Alternatively, cells with a reconstituted SSA marker may be enriched or purified using a drug selection scheme wherein the reconstituted SSA marker encodes a resistance marker. Cells may also be enriched using magnetic beads wherein the beads contain a ligand or antibody to a reconstituted cell surface protein or receptor.

In addition, the methods and compositions of the invention can be used to increase targeted insertion of a sequence of interest. Cells can be modified with one or more of the desired nuclease in the presence of the reporter and a donor sequence wherein following successful DNA cleavage by the nuclease, the donor sequence is incorporated either by homology-directed repair (HDR) or capture by end-joining.

Methods and compositions described herein are also used in kits suitable for the identification, isolation and optimization of nucleases as well as for targeted nucleic acid insertion or deletion into the genome of a cell.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains or TAL-effector domain nuclease fusion proteins.

EXAMPLES

Example 1

Preparation of Zfns

ZFNs targeted to CCR5, GFP, WAS and Factor IX were designed and incorporated into plasmids vectors essentially as described in Urnov et al. (2005) *Nature* 435(7042):646-651, Perez et al (2008) *Nature Biotechnology* 26(7): 808-816, and United States Patent Publication No: 2008/0131962 or were obtained from Sigma Aldrich. These ZFNs were constructed and tested by ELISA and the Surveyor™ (Transgenomics) Cel-1 assay ("Cel-1") as described in Miller et al. (2007) *Nat. Biotechnol.* 25:778-785 and U.S. Patent Publication No. 20050064474 and International Patent Publication WO2005/014791. In addition, see U.S. Provisional Application No. 61/212,265 relating to ZFNs targeted to Factor IX, and United States Patent Publication No: 2008/0159996 relating to CCR5-specific ZFNs.

Example 2

Generation and Testing of a SSA Reporter Construct

A single-stranded annealing (SSA) reporter construct was assembled with two halves of the gfp gene separated by ZFN binding sequences in the middle (FIG. 1A). Briefly, in this construct, 430 base pairs (bp) of the first half at the 3' end are identical to 430 bp of the 5' sequence of the second half. The first half has 146 bp unique sequences starting with the first Met codon ATG and the second half has 146 unique by ending with the stop codon. The ZFN binding sequence in the middle changes depending on the target sequence of ZFNs to be tested. One or more ZFN binding sites can be inserted into the construct allowing one reporter construct to be used for screening more than one nuclease. For example, a construct may contain the target sequence for a control pair of ZFNs as well as the target for an unknown nuclease. A CMV promoter lies in front of the gfp sequence and a polyA sequence follows the second half of the gfp sequence. This plasmid also contains a Kanamycin resistance gene for propagation in bacteria.

A CCR5-specific ZFN binding site was inserted into the SSA reporter described above and GFP activity assayed in CHO-S cells following transfection by Amaxa nucleofection with the reporter construct and a pair of ZFNs targeting the inserted sequence. Reporter activity was measured as percentage of cells expressing GFP.

Figure 1B:
FIG. 1B is a graph depicting ZFN dosage optimization in CHO-S cells. One million CHO-S cells were transfected by Amaxa nucleofection with various amounts of CCR5-specific ZFNs and 500 ng of a CCR5-specific SSA reporter. Samples were assayed 3 days after transfection and signal was measured as percentage of gfp+ cells.
Figure 1C:
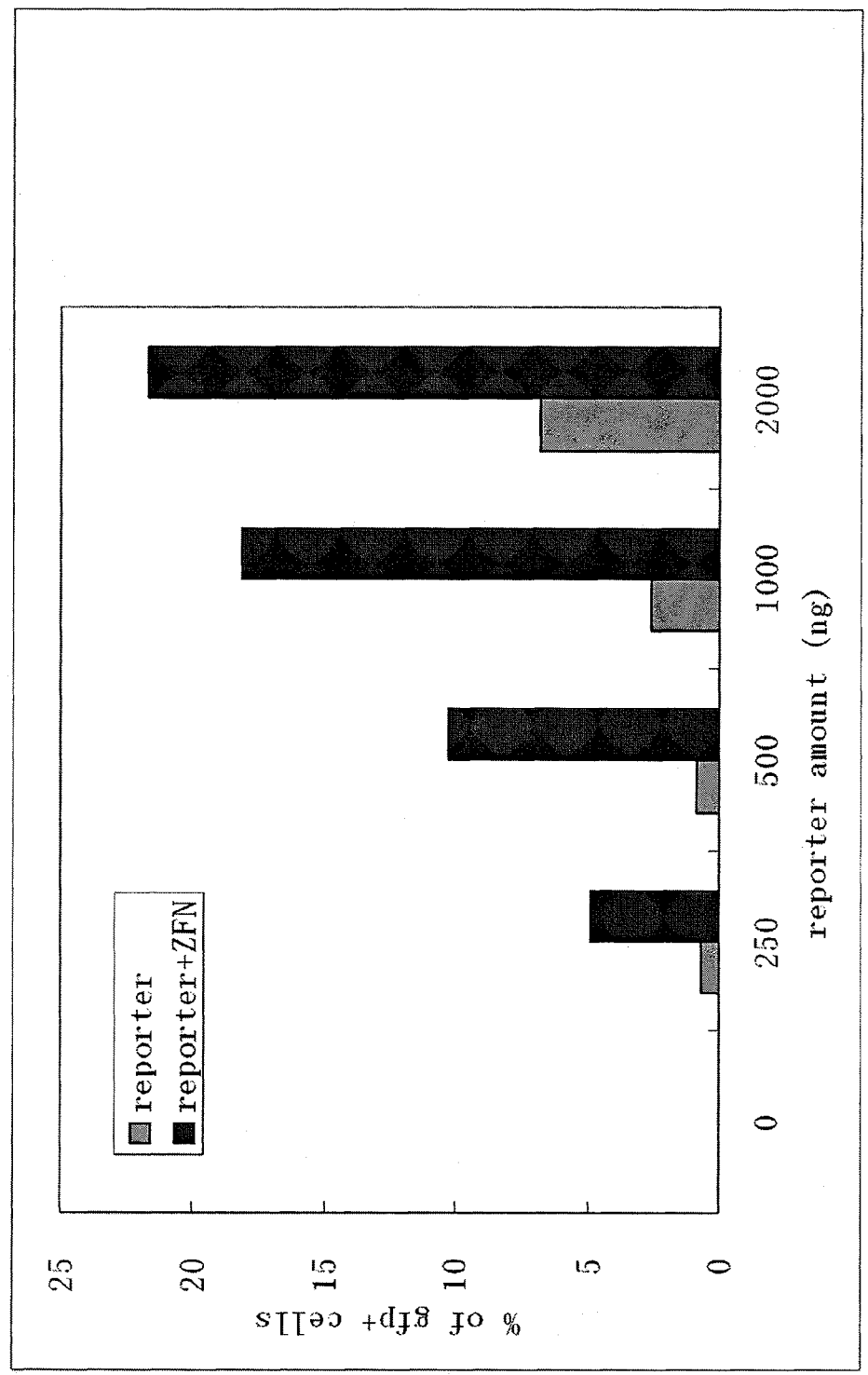
FIG. 1C is a graph depicting reporter dosage optimization of a ZFN screening assay in CHO-S cells. CHO-S cells transfected with various amount of the reporter plasmid and 1 µg of a CCR5 ZFN plasmid were assayed 3 days after transfection and signal was measured as percentage of gfp+ cells by Guava analysis. Bars on the left of each set of two bars show cells transfected with reporter alone while bars on the right show cells transfected with reporter and ZFNs.
Figure 1D:
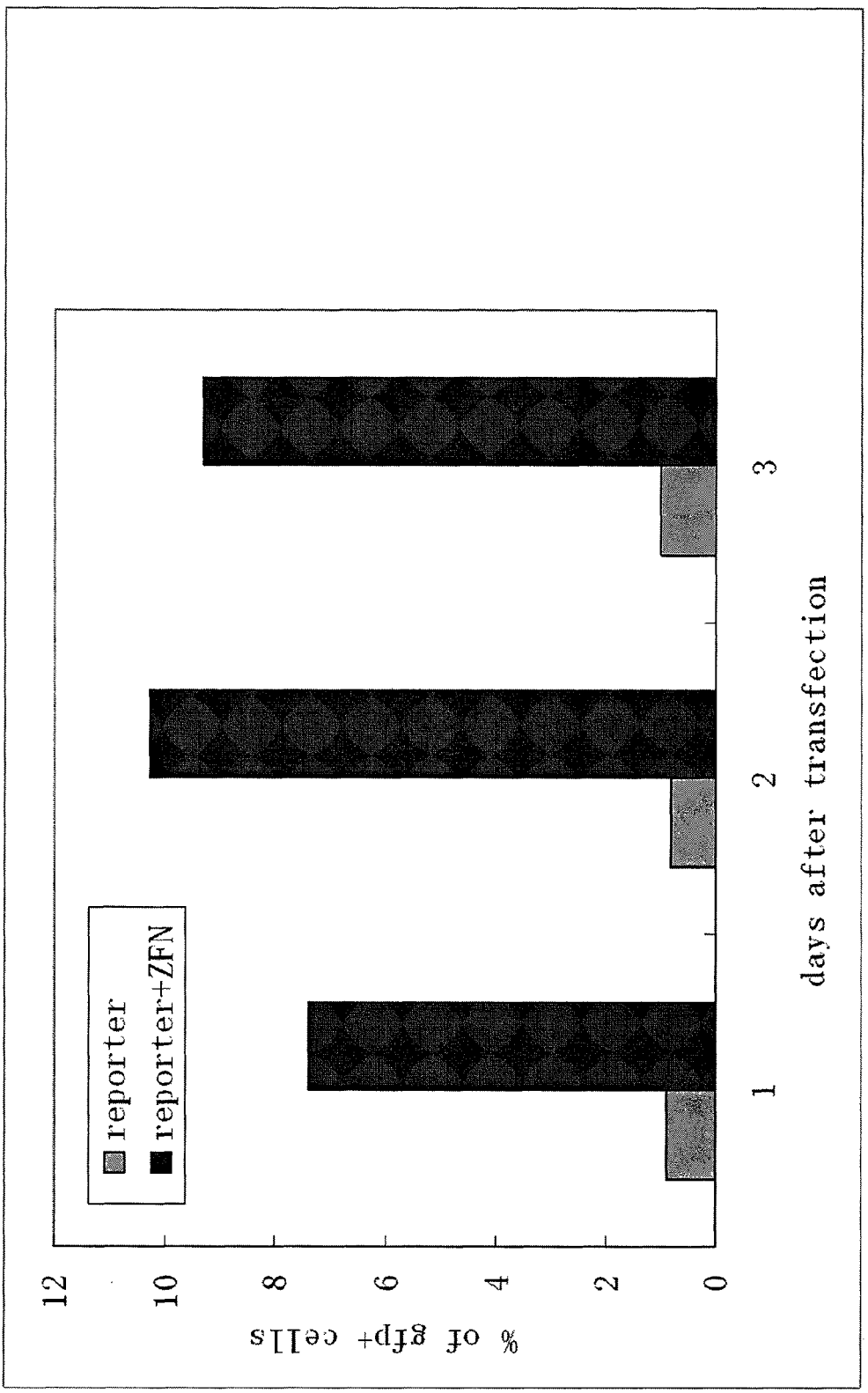
FIG. 1D is a graph depicting the time course of the ZFN screening assay. The gfp signal of samples transfected with 1 µg of a CCR5 ZFN and 500 ng of the SSA reporter was measured at day 1, 2, and 3 after transfection. Bars on the left of each set of two bars show cells transfected with reporter alone while bars on the right show cells transfected with reporter and ZFNs.

As shown in FIGS. 1B and 1C, this assay showed a good dose response to both the amount of ZFN and the amount of SSA reporter (FIGS. 1B and 1C). The GFP signal is most robust 48 to 72 hours after transfection (FIG. 1D). The optimal amount of ZFN and GFP-SSA reporter construct determined were used in subsequent experiments.

Example 3

Correlation of ZFN Activity on the SSA Reporter with Endogenous NHEJ Activity

The correlation between ZFN activities on the SSA reporter with that at the endogenous target sequence in the genome was also determined. Briefly, a reporter as described in Example 2 was generated with multiple ZFN target sites of the human WAS gene (NCBI GeneID: 7454) and evaluated for GFP expression upon introduction of the appropriate ZFNs expression plasmids. Briefly, K562 cells were transfected with optimized amount of ZFN expression plasmid and a WAS GFP-SSA reporter construct. A third of the cells were taken 2 days after transfection and GFP signal was measured. The rest of the cells were harvested 3 days after transfection and were used to analyze NHEJ activity at the endogenous WAS gene as a result of ZFN treatment, where NHEJ activity was assayed with the Surveyor™ nuclease as described, for example, in U.S. Patent Publication Nos. 20080015164; 20080131962 and 20080159996 (hereafter referred to as the "Cel-1 assay").

Figure 2:
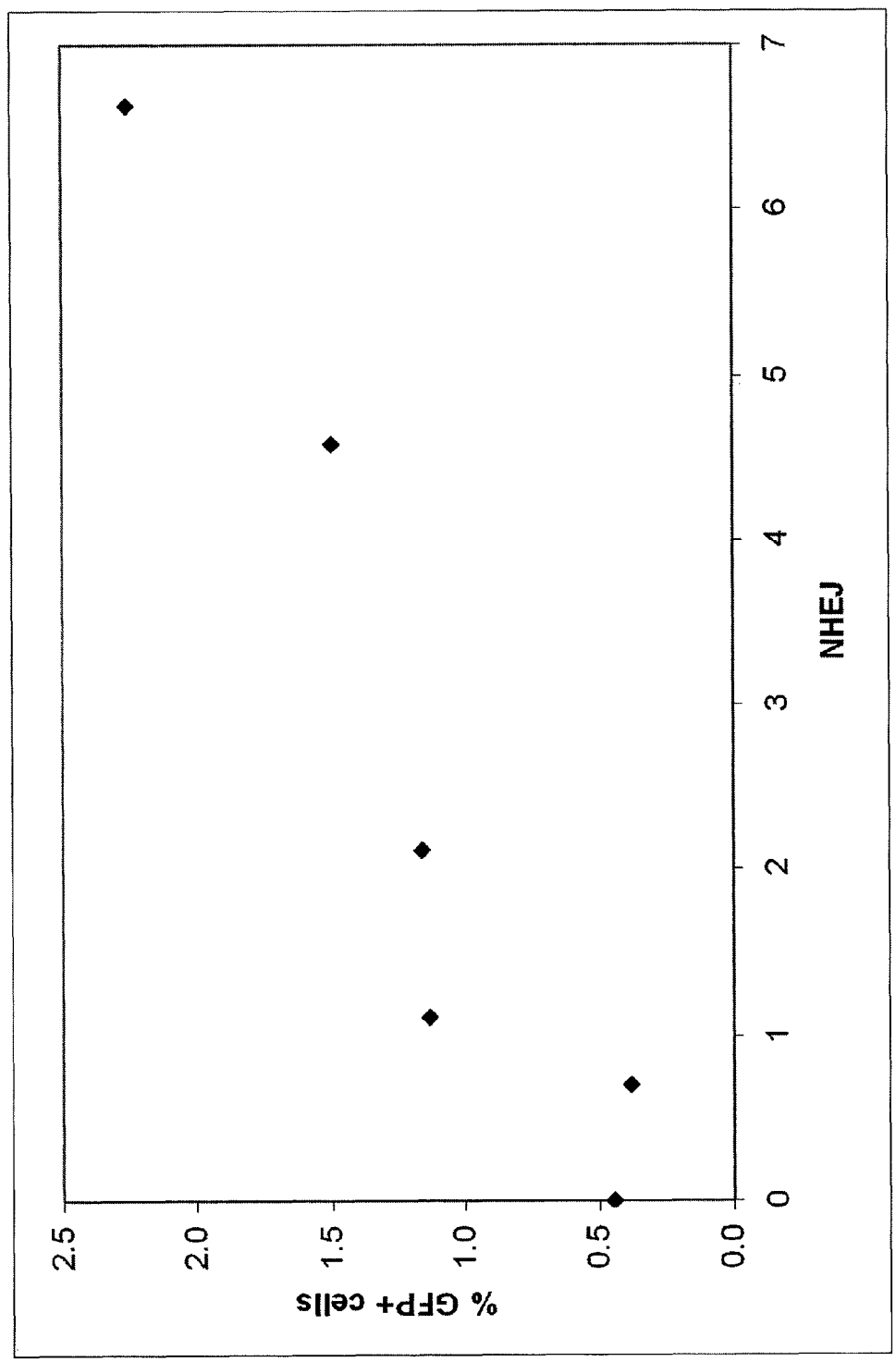
FIG. 2 depicts the correlation of ZFN activity as determined using the SSA assay (using the GFP reporter read out) to NHEJ activity of the nuclease. NHEJ activity is expressed as percentage of gene modification. The data demonstrates that GFP signal increases as NHEJ activity increases.

As shown in FIG. 2, there is a strong positive correlation of ZFN activity on the reporter construct and at the desired target locus in the endogenous site.

Example 4

Enrichment for ZFN-Modified Cells

Given the strong positive correlation of ZFN activity on the reporter construct and at the endogenous target site, it was presumed that cells that undergo SSA (as determined by correction of the GFP reporter) are expressing a sufficient amount of ZFNs to cleave the endogenous target locus and therefore induce repair of a double-stranded break (DSB repair).

K562 cells were transfected with ZFN targeting the Factor IX gene and the appropriate SSA reporter construct (containing the Factor IX ZFN target sequence) and then were sorted by FACS 3 days after transfection. ZFN and reporter construct transfected K562 cells were stained with propidium iodide (PI) for 5 minutes before FACS analysis. Gated FACS analysis showed that 0.3% the population expressed the highest levels of GFP, 0.9% of the population expressed mid level amounts of GFP and 2.3% of the cells expressed GFP at lower, but still detectable levels.

Figure 3:
FIG. 3 shows a gel depicting NHEJ activity before and after FACS sorting in K562 cells. Cel-I analysis was performed on cells transfected with the GFP plasmid alone (G) and cells transfected with plasmids expressing Factor IX-specific ZFNs and a reporter, where the cells were either sorted based on reporter activity (S), or left unsorted (U). Lane numbers are marked at the bottom of the gel. Lane 1 is a marker (M) and lane 2 is blank. The sorted lane shows an increase in ZFN activity in comparison with either cells that did not receive the nuclease or the unsorted population of cells.

As shown in FIG. 3 and Table 1 below, NHEJ activity, as determined via the Cel-1 assay, was increased in both FACS sorted (S) and unsorted (U) cells in the presence of the ZFN, as compared to cells transfected with the reporter plasmid only (G). Sorted cells showed higher NHEJ activity (see FIG. 3 and Table 1 below).

TABLE 1

| Sample | NHEJ (%) |
| --- | --- |
| GFP reporter alone (G) | 0.26 |
| GFP reporter + ZFN (FACS sorted) | 40.79 |
| GFP reporter + ZFN (unsorted by FACS) | 17.90 |

The SSA reporter system was also tested in HeLa cells and PBMC cells with CCR5-specific ZFNs. Briefly, experiments were conducted as described above for K562 cells in HeLa cells. In addition, PBMC cells were transduced with adenoviruses expressing CCR5-specific ZFNs and a GFP-SSA reporter construct.

Figure 4:
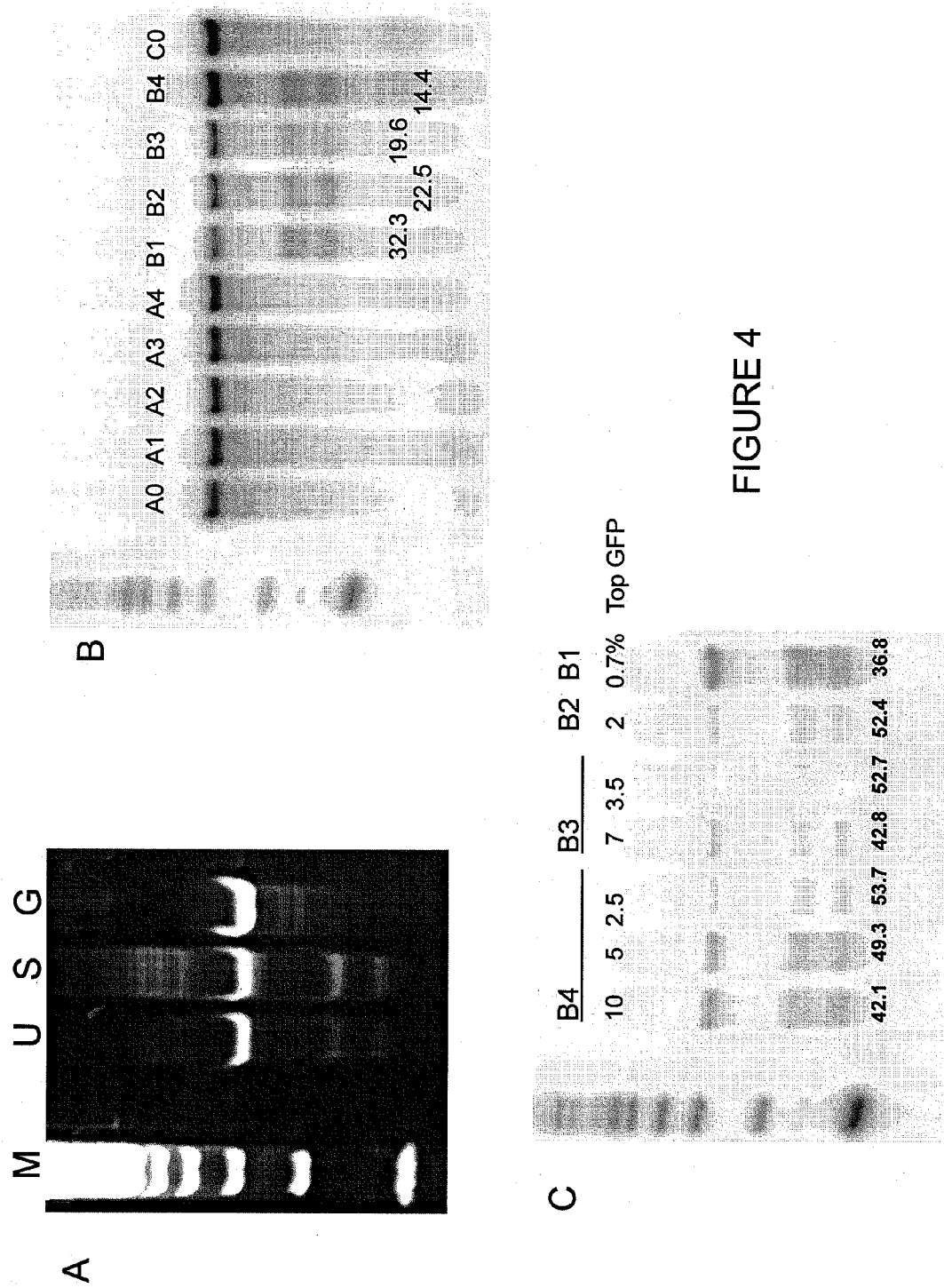
FIG. 4, panels A to C, depict enrichment of NHEJ activity in Hela cells and PBMCs by ZFNs.

As shown in FIG. 4A and Table 2 below, there was a ~2 fold enrichment of NHEJ activity as determined by the Cel-1 assay, in the sorted pool of HeLa cells.

TABLE 2

| Sort | NHEJ (%) |
| --- | --- |
| Pre (U) | 5.90 |
| Post (S) | 13.30 |

Similarly, when the GFP positive cells are sorted and analyzed, there was a quantitative correlation between the SSA signal and the NHEJ activity in both HeLa cells (FIG. 4B) and PBMC (FIG. 4C). Higher GFP signal in the sorted pool correlates with more endogenous gene modification. Furthermore, the SSA reporter assay was also successfully tested in Hep3B, 293T, and T cells. In general, a 2 to 6 fold of enrichment of NHEJ activity with different ZFNs was observed in all cell types that displayed high reporter activity. NHEJ activity was absent in cell samples that had been transduced with reporter only (lanes A0-A4). Four different cell samples from cells transduced with the ZFNs and the GFP-SSA reporter construct all showed evidence of NHEJ activity as determined by the Cel-1 assay (see lanes B1-B4). Percent NHEJ activity is indicated at the bottom of lanes B1-B4 and ranges from 14.4-32.3%.

These data demonstrate that this SSA based assay can be used in a variety of cell lines to screen ZFNs, to optimize reaction conditions, to enrich modified cells, and to efficiently derive modified cell clones using a variety of viral and non-viral nucleic acid delivery methods.

Example 5

Isolation of Cell Clones with all Copies of Target Gene Disrupted

Single cell cloning of ZFN modified knock-out cells by standard limiting dilution can require the screening of hundreds, if not thousands, of clones. Using conventional gene targeting strategies to knockout a gene without the aid of ZFNs may take several rounds of screening wherein the investigator must screen >100,000 cell clones. Therefore, we further tested if it is possible to efficiently isolate knockout cell clones by enriching for cells that had successfully reconstituted the reported gene by SSA.

At day 3 following transduction, single cells that had been transduced with the Factor-IX-specific ZFN expression vector and the GFP-SSA reporter construct as described in Example 4 were FACS sorted into 96-well plates based on GFP activity. Clones sorted from three different GFP gates (low, mid, high), and following nucleic acid extraction, were genotyped by TOPO cloning of the PCR product of the targeted allele followed by sequencing analysis. There are three types of clones: wild type (WT), heterozygous (HET), and knockout (KO). Sequencing analysis showed a very high percentage of the clones are complete "knock-out" clones with all copies of the target sequence disrupted (Table 3 below). In addition, clones were FACS analyzed for GFP expression 41 days after transfection. Results are shown in Table 3 below.

TABLE 3

FACS/SSA clone information

| GFP gating | clone | genotype | GFP signal at day 41 |
|---|---|---|---|
| Low | P096 | KO | − |
| Low | P097 | KO | − |
| Low | P098 | KO | − |
| Low | P099 | WT | − |
| Low | P100 | WT | − |
| Medium | P101 | KO | − |
| Medium | P102 | HET | − |
| Medium | P103 | KO | − |
| High | P104 | KO | − |
| High | P105 | KO | − |
| High | P106 | KO | + |
| High | P107 | KO | − |

The genotypes of 31 SSA/CCR5-specific ZFN-modified HeLa cell clones were also determined as set forth above. Of these clones, 13 exhibited wild type (WT) genotype, 11 were heterozygous (HET) for ZFN modifications and 7 were knockouts (KO).

Thus, the frequency of modifications isolated following SSA mediated FACS sorting, based on reconstituted reporter activity followed by single cell cloning, is much higher than standard limiting dilution screening.

Example 6

Enrichment and Isolation of Cells with ZFN-Mediated Targeted Insertion

Endogenous targets have been modified by targeted insertion of an exogenous sequence (donor molecule) perhaps using homology directed repair (HDR) mediated by a ZFN. See, e.g., U.S. Patent Publication No. 20070134796.

Accordingly, the SSA assay was tested to determine if it could be used to enrich such targeted integration events as follows. K562 cells were transfected using standard techniques with a small "patch" donor molecule in addition to CCR5-specific ZFNs and a GFP-SSA reporter construct. The "patch" donor included 51 bp exogenous sequence between the two ZFN binding sites and was flanked by CCR5 gene sequence on both sides, which served as arms of homology for introducing the patch donor into the endogenous CCR5 locus. The patch donor also included a novel BglII restriction site for PCR based restriction fragment length polymorphism (RFLP) analysis (see Urnov et. al. (2005) *Nature* 435:646-651. Moehle et. al. (2006) *PNAS* 104:3055-3060; U.S.).

Figure 5:
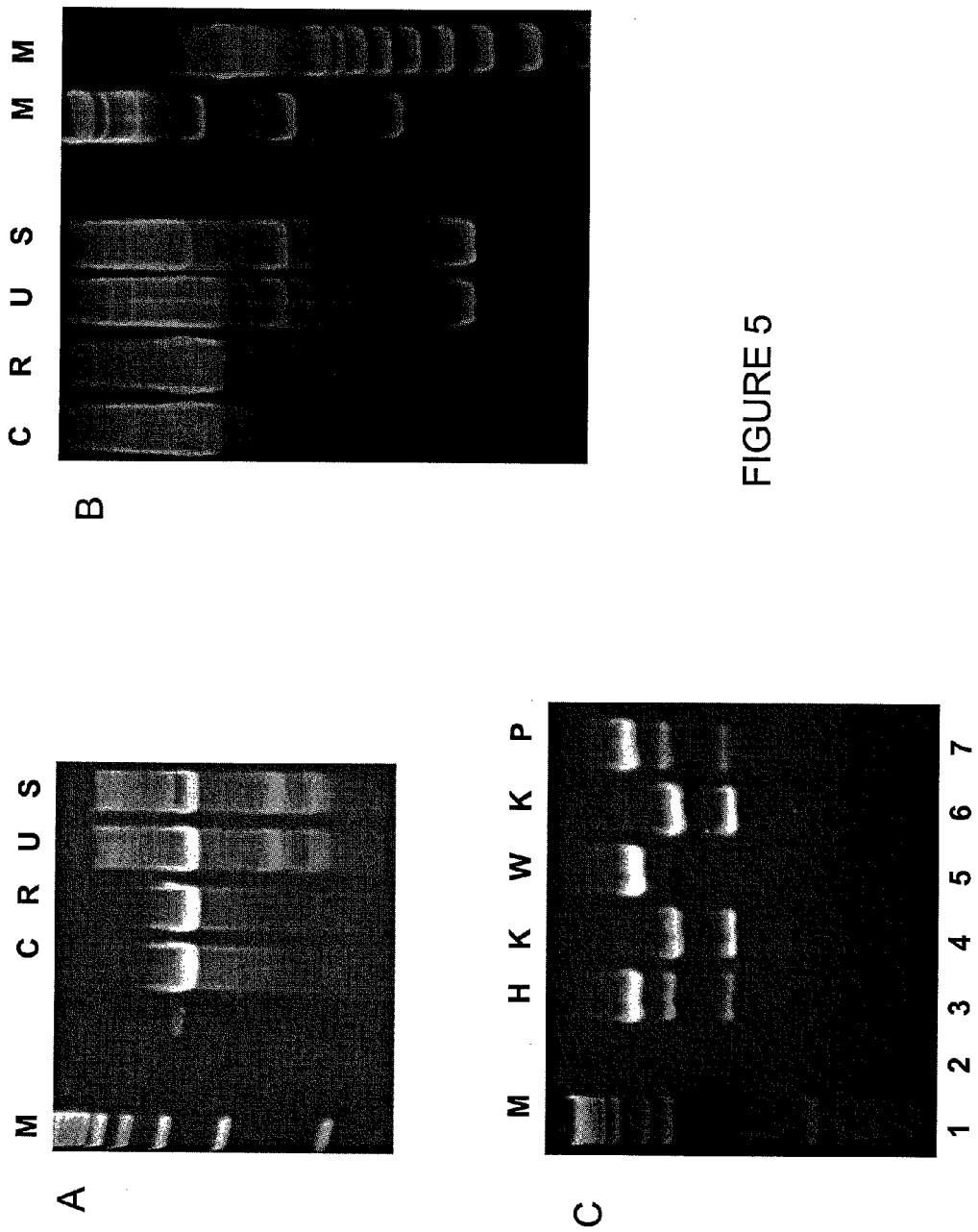
FIG. 5, panels A to C, are gels depicting enrichment and isolation of K562 cell clones with targeted integration.

As shown in FIGS. 5A and 5B and Table 4 below, NHEJ activity, as determined by the Cel-1 assay, was increased in both FACS-sorted and unsorted cells (FIG. 5A) in comparison with control reactions of either a mock transfection (no DNA) or a reporter construct only transfection (no ZFNs). In addition, targeted integration of the patch donor was also increased in both sorted and unsorted cells as compared to controls (FIG. 5B). When cell pools were sorted according to GFP activity, there was an increase observed in both the percent of NHEJ and in the percent of HDR. These results are also shown in Table 4 below.

TABLE 4

| Sample | ZFN | GFP signal | NHEJ (%) | HDR % |
|---|---|---|---|---|
| Mock (C) | − | − | 0.0 | 0.0 |
| Reporter (R) | − | + | 0.0 | 0.0 |
| Unsorted (U) | CCR5 | + | 25.0 | 37.5 |
| Sorted (S) | CCR5 | + | 37.5 | 72.0 |

Thus, when sorted and unsorted samples are compared, cells that had undergone targeted insertion of the patch sequence via HDR mediated targeted integration (TI) can be enriched by this method.

In addition, single cell clones with the desired targeted integration (TI) event were isolated as follows. 3 days after transfection, single cells were sorted into 96-well plates according to the gated gfp signal and allowed to grow. PCR based RFLP analysis described above was used to genotype the clones.

As shown in FIG. 5C and Table 5 below, wild type clones do not have the indicative Bgl II bands (lane 5 of FIG. 5C, labeled "W"), while clones with all alleles modified showed the only fully digested bands (lanes 4 and 6 of FIG. 5C, labeled "K"). Clones heterozygous for this modification showed partial digestion (lane 3 of FIG. 5C, labeled "H"), indicative of both the wild type allele and the allele containing the inserted donor patch containing the Bgl II restriction site. As is shown in Table 5, the identification of cells in which TI had occurred was much higher (7 out of 10 lines examined showed some TI activity) as compared to standard limited dilution screening.

TABLE 5

| Genotype | Number of Clones |
|---|---|
| Wild type | 3 |
| TI - heterozygous | 4 |
| TI - homozygous | 3 |

These results demonstrate that the methods and compositions described herein can be used to enrich and isolate cells with ZFN-mediated targeted integration events at a high frequency.

Example 7

Comparison of SSA Enrichment and Enrichment Using GFP Expression

As determined above (see, e.g., Example 4), enrichment for ZFN-modified cells can be achieved by sorting cells for expression of a functional SSA reporter. Accordingly, enrichment capability of SSA sorting as compared to enrichment by GFP expression was compared as follows.

K562 cells were transfected with a ZFN expression plasmid along with a gfp expression plasmid to mimic the GFP expression level achieved using the ZFN-mediated reconstituted GFP-SSA reporter system. Cells transfected with the ZFN expression plasmid, and then either with the GFP expression plasmid or with GFP-SSA reporter were sorted by FACS with identical settings 3 days after transfection.

Figure 6:
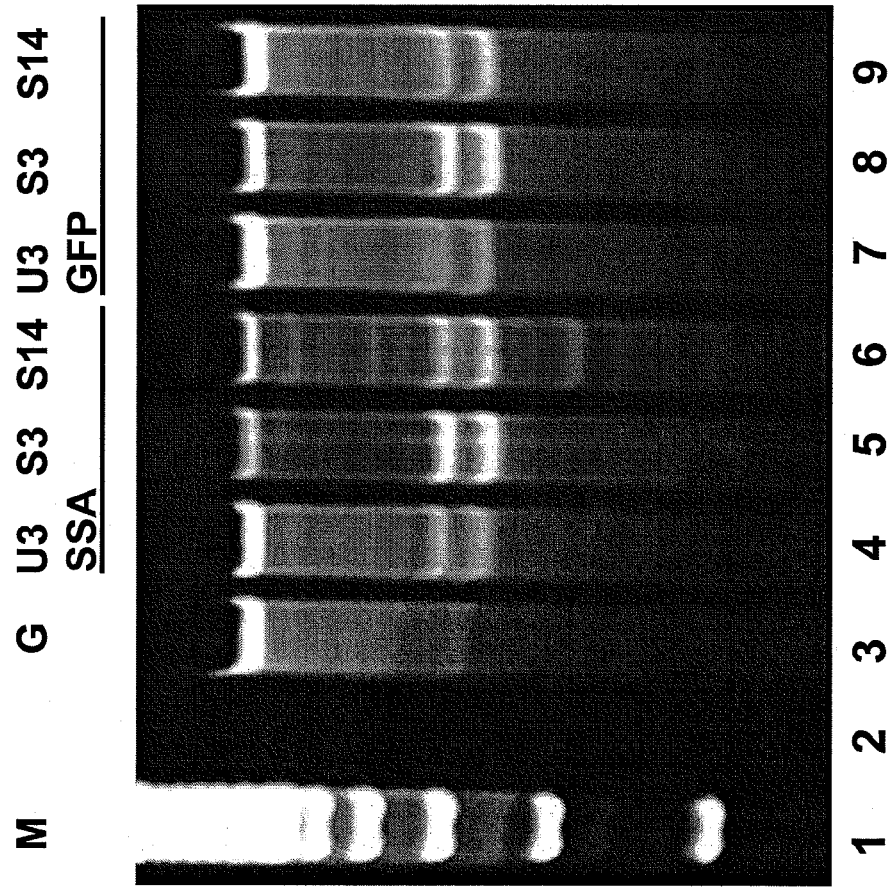
FIG. 6 depicts comparison of enrichment of NHEJ activity of ZFNs as measured by the Cel-1 assay at day 3 and day 14 after transfection. Lane numbers are designated beneath the gel. As shown, lanes 4, 5, 6 are samples transfected with ZFN and the GFP-SSA reporter constructs, and then and sorted by GFP activity. Lanes 7, 8, 9 are samples transfected with a GFP expression plasmid, and also sorted by GFP activity. "U3" denotes samples pre-sorted at day 3. "S3" denotes samples post-sorted at day 3. "S14" denotes samples sorted at day 14 sorted sample at day 14 post-transfection.

Cells sorted by GFP activity as a result of the reconstitution of the gfp gene in the GFP-SSA reporter construct showed higher level of enrichment 3 days after transfection and the activity was retained at a higher level at a later time point (day 14) (FIG. 6) as compared to the transfectants that received the GFP expression plasmid. Furthermore, single cell clones derived from SSA reporter sorting showed a higher frequency knockout clones (Table 6) than those transfectants that received the GFP expression vector.

TABLE 6

| NHEJ (day 3) | NHEJ (day 14) | KO frequency | Sort | GFP source vector |
|---|---|---|---|---|
| 17.6 | ND | | pre | GFP-SSA |
| 52.2 | 41.8 | ½ | post | GFP-SSA |
| 15.3 | ND | | pre | GFP expression |
| 31.9 | 19.0 | 0/5 | post | GFP-expression |

These results demonstrate that sorting of cells expressing the SSA reporter provides superior enrichment for ZFN-modified cells.

Example 8

Reporter Expression

Because the methods described herein do not involve drug selection, the derived single cell clones are not expected to have the SSA reporter gene integrated into their genomes.

To evaluate this idea, Factor IX-specific ZFN clones were evaluated for GFP expression 41 days post-transfection. Only one clone (#106) retained GFP expression at 41 days post-transfection (see Table 3).

Figure 7:
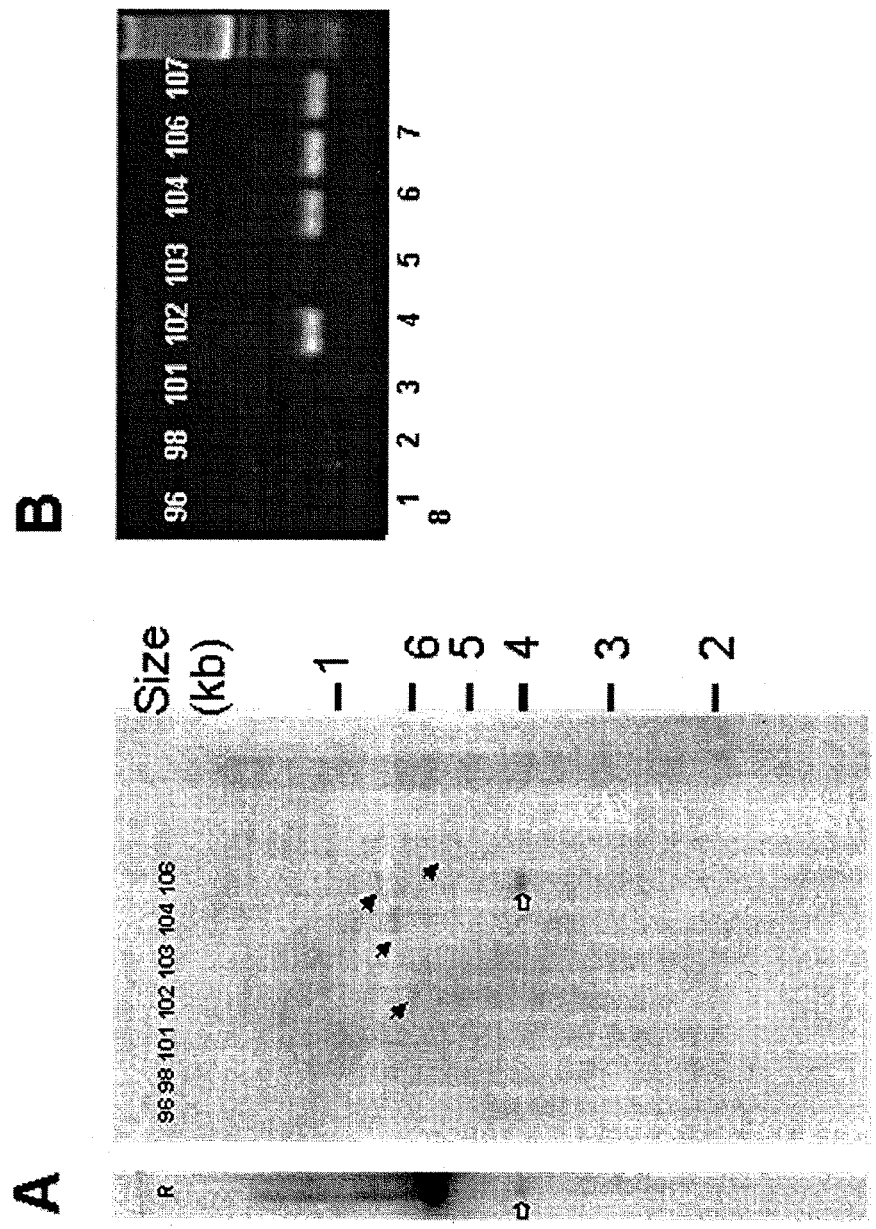
FIG. 7, panels A and B, depict analysis of Factor IX-targeted ZFN modified cell clones.

In addition, the presence/absence of the SSA reporter in the genome was further examined by Southern Blot and PCR analysis. For Southern Blot analysis, the clones were digested with PvuII and probed with the 146 bp of 5' unique gfp sequence. As shown in FIG. 7A, approximately half the clones (96, 98, 101 and 103) did not have a band corresponding to SSA reporter expression. These results were confirmed by PCR analysis (FIG. 7B) where gfp specific PCR primers were used in an effort to amplify any gfp sequence that had integrated into the genome.

Since nearly half of the clones do not show any evidence of reporter gene integration, this methodology can be easily used to isolate single cell clones without integrated reporter.

Example 9

High-Throughput Screening and Cloning

The SSA assays as described herein was also used to screen a large set of ZFNs that were specific for several different target genes where the ability to induce NHEJ at the target was compared to GFP-SSA reporter activity. The appropriate SSA reporter constructs for the ZFNs were generated as described above and tested as described above in K562 cells in 96-well plates. The number of ZFN pairs specific for particular target genes tested is listed in Table 7 as 'ZFN pairs'. ZFNs that gave a GFP signal yield higher than 50% of the CCR5-specific ZFNs signal were scored as positive. (see Table 7 below, "SSA+") The ZFNs were scored NHEJ positive if they showed >1% NHEJ activity. Cells that showed GFP activity but did not show any evidence of NHEJ were deemed 'false positive' while those with less that 50% of the CCR5-specific ZFN activity while having evidence of NHEJ by the Cel-1 assay were termed 'false negative'. The two assays were then used to rank the ZFN pairs for each target.

The rankings as determined by NHEJ were compared to those rankings determined by the GFP-SSA reporter assay. See Table 7, last column. SSA rankings are indicated in parenthesis. In most cases, the SSA rankings and the NHEJ rankings were very similar.

As shown in Table 7, SSA based screening always correctly identified the positive hits as determined by NHEJ. In addition, the ZFNs that scored high in the SSA assay also tended to have higher NHEJ activity at the endogenous locus.

TABLE 7

| Target gene | ZFN pairs | SSA+ | NHEJ+ | % False+ | False− | NHEJ rank (SSA rank) |
|---|---|---|---|---|---|---|
| A | 16 | 9 | 7 | 22 | 0 | 1(1) |
| B | 19 | 12 | 11 | 8 | 0 | 1(2), 2(1) |
| C | 9 | 1 | 1 | 0 | 0 | 1(1) |
| D | 16 | 9 | 4 | 56 | 0 | 1(2), 2(1) |
| E | 8 | 6 | 5 | 17 | 0 | 1(5), 2(1), 3(2), 4(5) |
| F | 9 | 3 | 1 | 67 | 0 | 1(3), FP(1), FP(2) |
| G | 8 | 2 | 1 | 50 | 0 | 1(2), FP(1) |
| H | 9 | 7 | 5 | 29 | 0 | 1(1) |
| Total | 94 | 49 | 35 | 29 | 0 | |

*FP—false positive

The SSA reporter system was also used to derive single cell clones in a high throughput fashion. Briefly, K562 cells were transfected with a panel of ZFNs targeting different genes and their corresponding SSA reporter constructs in 96-well format using Amaxa Shuttle. The NHEJ activity of the ZFNs were determined by the Cel-I assay 3 days after transfection. Cells were FACS sorted also 3 days after transfection into individual clones on 96-well plates. When the clones grew up, they were genotyped as described in Example 5 by PCR amplification of the target sequence followed by cloning and sequence analysis of the PCR product. Cell clones without any unmodified copy of the ZFN target sequence are designated KO clones. The frequency of KO clones of all clones analyzed are listed as the last column of Table 8.

The results are summarized in Table 8.

TABLE 8

| Target gene | NHEJ (%) | Total clones | KO clones | KO frequency |
|---|---|---|---|---|
| CCR5 | 20.0 | 4 | 1 | 25.0 |
| WAS | 17.9 | 2 | 1 | 50.0 |
| Factor IX | 17.0 | 12 | 9 | 75.0 |
| I | 17.0 | 5 | 3 | 60.0 |
| J | 14.2 | 5 | 3 | 60.0 |
| K | 11.0 | 13 | 2 | 7.1 |
| L | 4.7 | 47 | 21 | 44.7 |
| M | 2.7 | 30 | 2 | 6.7 |

To test the generality of this approach, we used ZFNs with different NHEJ activities to derive KO clones. The NHEJ activity range from 20.0% down to 2.7%. These results show that the ZFN/SSA assay system described herein can be used to screen and isolate ZFN-modified cell clones with NHEJ activity as low as 2.7%, and the frequency of the identification of knockout clones is much higher than standard limiting dilution.

Example 10

Enrichment of Cells Using a Antibiotic Resistance SSA Reporter

A SSA reporter gene was constructed using the puromycin gene. In this construct, the puromycin SSA reporter was build similarly to the GFP SSA reporter described above. The first 452 bp and last 422 bp of the puromycin resistance gene were interlinked with the ZFN targeting sites. In this example, the ZFN used targets the CHO Bax gene (see, U.S. patent application Ser. No. 12/456,043).

Figure 8:
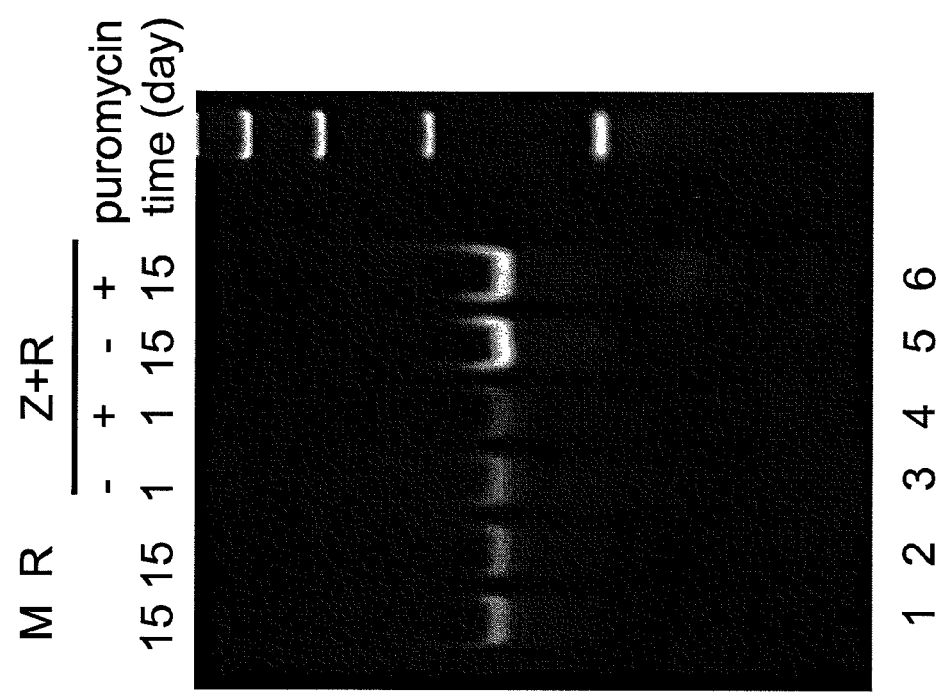
FIG. 8 depicts the results of CHO Bax-targeted ZFN modified HeLa cells using a puromycin SSA reporter. In this experiment, cleavage of the ZFN resulted in reconstituting a puromycin resistance gene. Cells were plated on puromycin 24 hours following transfection with the ZFN expression plasmid and the puromycin SSA reporter. Samples were collected after 1 or 15 days and used for mismatch analysis using the Cel-I assay. 'M' indicates mock transfected cells lacking a SSA reporter, 'R' indicates the use of the SSA reporter in the transfection. '+' or '−' indicates the presence or absence of puromycin in the media. Numbers at the bottom of the lanes indicate the amount of NHEJ that has occurred.

HeLa cells were transfected by Amaxa nucleofection with plasmids as indicated in FIG. 8. 500 ng of reporter and 400 ng of ZFNs were used per sample (M=mock, R=reporter, Z+R=ZFN and reporter). Cells were replated 24 hours after transfection in medium either with or without 1 μg/ml puromycin. Cell medium was replaced to regular medium 72 hours after transfection. Samples from different time point were collected and subjected to Cel-I assay analysis as described above. FIG. 8 shows a clear increase of NHEJ activity in SSA enriched sample 15 days after transfection, as measured by the Cel-I assay.

What is claimed is:

1. A host cell comprising an endogenous genome and an episomal reporter construct, the episomal reporter construct comprising a sequence consisting essentially of target sequences for multiple pairs of zinc finger nucleases, the target sequences flanked by sequences encoding a disabled reporter gene, wherein the target sequences are the same as sequences in the endogenous genome and further wherein the sequences encoding the disabled reporter comprise identical repeated sequences flanking the target sequences.

2. The host cell of claim 1, wherein the reporter construct further comprises a polyadenylation signal.

3. The host cell of claim 1, wherein the reporter construct further comprises a promoter sequence operably linked to the reporter gene.

4. The host cell of claim 3, wherein the promoter is selected from the group of consisting of a constitutive promoter, a regulatable promoter or inducible promoter.

5. The host cell of claim 1, wherein the reporter gene encodes a light-generating protein, an enzyme, a cell surface receptor, or a selectable marker.

6. The host cell of claim 1, wherein the cell is a eukaryotic cell.

7. The host cell of claim 6, wherein the cell is a mammalian cell.

8. The host cell of claim 1, wherein the reporter construct further comprises a regulatable promoter operably linked to the reporter gene.

9. The host cell of claim 1, further comprising a sequence encoding a nuclease, wherein the nuclease comprises a zinc finger protein.

10. The host cell of claim 1, further comprising a donor polynucleotide that is integrated into the endogenous genome.

11. A method of identifying one or more zinc finger nucleases that induce cleavage at a specific target site, the method comprising the steps of:
   introducing one or more expression constructs that expresses the zinc finger nuclease(s) into a host cell according to claim 1, wherein the reporter construct comprises a target sequence recognized by the nuclease(s);
   incubating the cells under conditions such that the zinc finger nuclease(s) are expressed; and
   measuring the levels of reporter gene expression in the cells, wherein increased levels of reporter gene expression are correlated with increased nuclease-induced cleavage of the target sequence.

12. A method of enriching a population of cells for cells having a nuclease-mediated genomic modification, the method comprising the steps of:
   introducing one or more expression constructs encoding one or more zinc finger nucleases targeted to recognize and cleave a target site in the genome into host cells according to claim 1, wherein the reporter construct in the host cells comprises the target sequence recognized by the nuclease(s);
   incubating the cells under conditions such that the nuclease(s) are expressed;
   measuring the levels of reporter gene expression in the cells; and
   selecting cells that express the reporter gene, thereby enriching the population of cells for cells with nuclease-mediated genomic modifications and an active nuclease.

13. The method of claim 12, further comprising isolating the cells expressing the reporter gene.

14. The method of claim 13, wherein the genomic modification is a gene disruption.

15. The method of claim 12, wherein the method further comprises introducing an exogenous sequence into the host cells such that it is incorporated into the genome.

16. The method of claim 15, wherein the genomic modification is a gene addition.

17. The method of claim 12, wherein the reporter gene encodes a fluorescent protein and the selecting comprises fluorescence activated cell sorting (FACS) analysis.

* * * * *